United States Patent
Grandi

(10) Patent No.: US 7,038,012 B1
(45) Date of Patent: May 2, 2006

(54) **ENRICHMENT PROCESS FOR *H. PYLORI* NEUTROPHIL ACTIVATING PROTEIN (NAP) UTILIZING METAL CHELATE CHROMATOGRAPHY**

(75) Inventor: Guido Grandi, Segrate (IT)

(73) Assignee: Chiron SRL, Siena (IT)

( * ) Notice: Subject to any disclaimer, the term of this patent is extended or adjusted under 35 U.S.C. 154(b) by 0 days.

(21) Appl. No.: 09/647,637

(22) PCT Filed: Apr. 7, 1999

(86) PCT No.: PCT/IB99/00695

§ 371 (c)(1),
(2), (4) Date: Oct. 12, 2000

(87) PCT Pub. No.: WO99/53310

PCT Pub. Date: Oct. 21, 1999

(30) Foreign Application Priority Data

Apr. 8, 1998 (GB) .................................. 9807721

(51) Int. Cl.
*C07G 7/00* (2006.01)
*A61K 39/12* (2006.01)

(52) U.S. Cl. ..................... 530/344; 530/350; 435/69.1; 424/184.1; 424/234.1

(58) Field of Classification Search ............. 435/252.1, 435/6, 188, 8, 7.32; 514/44, 12, 2; 530/412, 530/350, 300; 424/184.1, 205.1, 199.1, 228.1, 424/229.1, 208.1, 9.34, 70.14, 70.16, 204.1, 424/225.1, 207.1, 234.1, 130.1, 137.1, 141.1, 424/150.1, 193.1, 278.1, 434, 236.1; 518/726
See application file for complete search history.

(56) References Cited

U.S. PATENT DOCUMENTS

| | | | |
|---|---|---|---|
| 4,724,208 A * | 2/1988 | Brewer et al. .............. 435/188 |
| 5,079,228 A * | 1/1992 | Cohen et al. ................. 514/12 |
| 5,646,016 A * | 7/1997 | McCoy et al. ............. 435/69.7 |
| 5,665,868 A * | 9/1997 | Ramadoss et al. .......... 530/412 |
| 5,759,533 A * | 6/1998 | Baggiolini et al. ........ 424/85.1 |
| 5,780,040 A * | 7/1998 | Plaut et al. .............. 424/234.1 |
| 5,907,035 A * | 5/1999 | Guinn ........................ 530/412 |
| 5,972,336 A * | 10/1999 | Michetti et al. ......... 424/184.1 |

(Continued)

FOREIGN PATENT DOCUMENTS

EP 0887403 A2 * 12/1998

(Continued)

OTHER PUBLICATIONS

Jin, DY et al, Chemistry, life sciences & earth sciences (China), Oct. 1993, vol. 36(10),pp. 1224-1232 (abstract only).*

(Continued)

*Primary Examiner*—Nita Minnifield
*Assistant Examiner*—Ginny Allen Portner
(74) *Attorney, Agent, or Firm*—Rebecca M. Hale; Felicity E. Groth; Alisa A. Harbin

(57) ABSTRACT

The invention relates to a process for enriching the presence of *H. pylori* NAP in a mixture of proteins. The process involves salting-out other proteins. NAP has been found to remain soluble at ammonium sulphate concentrations of 80% and above. The process may involve the additional step of metal chelate chromatography. The combination of salting-out and metal chelate chromatography results in very pure NAP. The NAP may have the same sequence as NAP naturally occurring in *H. pylori* and is free from sequences typically associated with recombinant protein production. The processes and NAP of the invention can be used in diagnostic and therapeutic products and processes.

13 Claims, 8 Drawing Sheets

U.S. PATENT DOCUMENTS

| | | | | | |
|---|---|---|---|---|---|
| 5,972,348 | A | * | 10/1999 | Plaut et al. | 424/234.1 |
| 6,054,132 | A | * | 4/2000 | Cover et al. | 424/236.1 |
| 6,124,271 | A | * | 9/2000 | Iversen et al. | 514/44 |
| 6,290,962 | B1 | * | 9/2001 | Michetti et al. | 424/185.1 |
| 6,383,479 | B1 | * | 5/2002 | Aschauer et al. | 424/85.1 |
| 6,534,064 | B1 | * | 3/2003 | O'Hagan et al. | 424/205.1 |
| 6,534,864 | B1 | * | 3/2003 | Tanaka et al. | 257/751 |
| 6,841,155 | B1 | * | 1/2005 | Del Giudice et al. | 424/184.1 |

FOREIGN PATENT DOCUMENTS

| | | | |
|---|---|---|---|
| WO | 90/06321 | | 6/1990 |
| WO | 92/01272 | | 1/1996 |
| WO | 92/01273 | | 1/1996 |
| WO | 96/01272 | * | 1/1996 |
| WO | 97/25429 | * | 7/1997 |
| WO | 99/53310 | * | 10/1999 |

OTHER PUBLICATIONS

Solca, FF et al, Journal of Biological chemistry, Nov. 4, 1994, vol. 269(44), pp. 27559-27565 (abstract only).*

Sylvester, I et al, american review of respiratory disease, Mar. 1990, vol. 141(3), pp. 683-688 (abstract only).*

Crabtree, JE et al, Scandinavian Journal of immunology, vol. 37(1), pp. 65-70, Jan. 1993, specifically p. 68, col. 1, paragraph 2.*

Evans, Doyle L. et al, Infection and Immunity, Jun. 1995, vol. 63(6), pp. 2213-2220, Characterization of *Helicobacter pylori* neutrophil activating protein.*

Evans, Doyle J. et al, Gene, vol. 153 (1995), pp. 123-127, Identification of four new prokaryotic bacterioferritins, from *Helicobacter pylori, Anabaena variabilis, BAcillus subtilis* and *Treponema pallidum* by analysis of gene sequences.*

McGowan C.C. et al, Gut, vol. 41(suppl. 1), pp. A18, 1997.*

Namavar, F et al, Infection and Immunity, vol. 66(2), pp. 444-447, Feb. 1998, Neutophil activating protein mediates adhesion of *Helicobacter pylori* to sulfated carbohydrates on High molecular weight salivary mucin.*

Teneberg, S et al, The Journal of Biological Chemistry, vol. 272(30), Jul. 25, 1997, pp. 19067-19071, Carbohydrate binding specificity of the neutrophil activating protein of *Helicobacter pylori*.*

Takacs, Bela J et al, Journal of Immunological Methods, vol. 143, pp. 231-240, 1991, Preparation of clinical grade proteins produced by recombinant DNA technologies.*

Takacs, Bela J et al, Journal of Immunological Methods, vol. 143, pp. 231-240, 1001, Preparation of clinical grade proteins produced by recombinant DNA technologies.*

Logan, RP et al, Gstroenterology, vol. 114(4 part 2), p. A1025, Apr. 15, 1998, The neutrophil activating protein of *Helicobacter pylori* is a DPS homologue without neutrophil activating properties.*

Namavar, F et al, Infection and Immunity, vol. 66(2), pp. 444-447, Feb. 1998, Neutrophil-Activating Protien mediates adhesion of *Helicobacter pylori* to sulfated carbohydrates on High Molecular weight salivary mucin.*

Worst, DJ. et al, Infection and Immunity, vol. 63(10), pp. 4161-4165, Oct. 1995, Iron Repressible outer membrane proteins of *Helicobacter pylori* involved in Heme Uptake.*

Andrews, SC et al, European Journal of biochemistry, Apr. 1, 1993, vol. 213(1), pp. 329-338, Overproduction, purification and characterization of the bacterioferritin of *Escherichia coli* and a C-terminally extented variant (abstract only).*

Laulhere, JP et al, Biochemical journal, Feb. 1, 1992, vol. 281(pt 3), pp. 785-793, Purification, characterization of bacterioferritin from the cyanobacterium Synechocystis P.C.C. 6803 (abstract only).*

Clerte, S et al, ACTA Crystallographica, Section D, vol. D55, pp. 299-301, 1999, Expression, purification, crystallization and preliminary X-ray diffraction results from *Campylobacter jejuni* ferritin.*

Nielsen, H et al, Gut, vol. 33(6), pp. 738-742, 1992, Chemotactic activity of *Helicobacter pylori* sonicate from human polymorphonuclear leucocytes and monocytes.*

Pessolani, Maria Cristina V et al, J. Exp. Med, Jul. 1994, vol. 180, pp. 319-327, Purification, characterization, gene sequence, and significance of a bacteriferritin from *Mycobacterium leprae*.*

Namavar, F et al, Infection and Immunity, Feb. 1998, vol. 66(2), pp. 444-447, Neutrophil activating protein mediates adhesion of *Helicobacter pylori* to sulfated carbohydrates on high molecular weight salivary mucin.*

Worst, D.J. et al, Infection and Immunity, vol. 63(10), pp. 4161-4165, Oct. 1995, Iron-repressible outer membrane proteins of *Helicobacter pylori* in Heme uptake.*

Bennedsen, M et al, Purification of chemotactic factors from *H.pylori,* Gut, vol. 41(suppl. 1) p. A113 (abstract 10/418), Sep. 11-14, 1997, European *Helicobacter pylori* Study Group Xth Lisbon Portugal.*

Yoshida, N et al, Gastroenterology, Nov. 1993, vol. 105(5), pp. 1431-1437, 1439 Mechanisms involved in *Heliboacter pylori* induced inflammation.*

Nielsen, H e al Gut, 1992, vol. 33, pp. 738-742.*

Pessolani, MC et al, J. Exp. Med. vol. 180, Jul. 1994, pp. 319-327.*

Mai, Uwe E.H. e tal, The Journal of Exp. Med. vol. 175, pp. 517-525, Feb. 1992.*

Satin, Barbara et al, J. Exp. Med. vol. 191, No. 9, pp. 1467-1476, May 1, 2000, The Neutrophil Activating protein (HP-NAP) of *Helicobacter pylori* is a protective antigen and a major virulence factor.*

Teneberg, S et al, The Journal of Biological Chemistry, vol. 272, No. 30, Jul. 25, 1997, pates 19067-19071, Carbohydrate binding specificity of teh neutrophil activating protein of *Helicobacter pylori*.*

Tufano, MA et al, Infection and Immunity, vol. 62(4), Apr. 1994, pp. 1392-1399, Immunological Activities of *Helicobacter pylori* porins.*

Bellini, A. V. et al., "Production processes of recombinant IL-β from *Bacillus subtilis*: comparison between intracellular and exocellular expression," *J. Biotechnol,* 1991, 18, 177-192.

Marchetti, M. et al., "Development of a mouse model of *Helicobacter pylori* infection that mimics human disease," *Science,* 1995, 267, 1655-1658.

Patent Abstract of Japan, vol. 006, No. 231 (C-135), JP 57132880, Nov. 17, 1982.

Sulkowski, E., "Purification of proteins by IMAC," *TIBTECH,* 1985, 3(1), 1-7.

Telford, J. L. et al., "Immunobiology of *Helicobacter pylori* infection," *Curr Opin Immunol,* 1997, 9, 498-503.

Telford, J. L. et al., "Unravelling the pathogenic role of *Helicobacter pylori* in peptic ulcer: Potential new therapies and vaccines," *TIBTECH,* 1994, 12, 420-426.

Tomb, J-F. et al., "The complete genome sequence of the gastric pathogen *Helicobacter pylori,*" *Nature,* 1997, 388, 539-547.

* cited by examiner

```
                                              SEQ ID NO 1
        SEQ ID NO 9                  
              Promoter    SacI  RBS
        ttttatgtaataatagattcataattgagagctctagagggtattaataATGAAAACA
                                                         MetLysThr
                                                         SEQ ID NO 2

SEQ ID NO 1   TTTGAAATTTTAAGACATTTGCAAGCGGATGCGATCGTGTGTTTATGAAAGTGCATAAC
SEQ ID NO 2   PheGluIleLeuArgHisLeuGlnAlaAspAlaIleValLeuPheMetLysValHisAsn

SEQ ID NO 1   TTCCATTGGAATGTGAAAGGCACCGATTTTTTCAATGTGCATAAAGCCACTGAAGAATT
SEQ ID NO 2   PheHisTrpAsnValLysGlyThrAspPhePheAsnValHisLysAlaThrGluGluIle

SEQ ID NO 1   TATGAAGAGAGTTTGCGGACACATGTTTGATGATCTCGCTGAAAGGATCGTTCAATTAGGACAC
SEQ ID NO 2   TyrGluGluPheAlaAspMetPheAspAspLeuAlaGluArgIleValGlnLeuGlyHis

SEQ ID NO 1   CACCCCTTAGTGACTTTATCTGAAGCACTCAAACTCACTCGTGTGAAAGAAGAAACTAAA
SEQ ID NO 2   HisProLeuValThrLeuSerGluAlaLeuLysLeuThrArgValLysGluGluThrLys

FIG. 1(A)
```

SEQ ID NO 1 ACGAGCTTCCACTCTTAAAGACATCTTTAAAGAAATTCTAGGCGATTACAAACACCTAGAA
SEQ ID NO 2 ThrSerPheHisSerLysAspIlePheLysGluIleLeuGlyAspTyrLysHisLeuGlu

SEQ ID NO 1 AAAGAATTTAAAGAGCTTTCTAACACTGCTGAAAAAGAAGGCGATAAAGTCACCGTAACT
SEQ ID NO 2 LysGluPheLysGluLeuSerAsnThrAlaGluLysGluGlyAspLysValThrValThr

SEQ ID NO 1 TATGCGGACGATCAATTGGCCAAGTTGCAAAAATCCATTTGGATGCTAGAAGCTCATTTG
SEQ ID NO 2 TyrAlaAspAspGlnLeuAlaLysLeuGlnLysSerIleTrpMetLeuGluAlaHisLeu

SEQ ID NO 1 GCTtaaaagctt
SEQ ID NO 2 AlaEnd
            HindIII

```
SEQ ID NO 2    1  MKTFEILKHLQADAIVLFMKVHNFHWNVKGTDFFNVHKATEEIYEEFADMFDDLAERIVQ
SEQ ID NO 5    1  MKTFEILKHLQADAIVLFMKVHNFHWNVKGTDFFNVHKATEEIYEEFADMFDDLAERIVQ
SEQ ID NO 6    1  MKTFEILKHLQADAIVLFMKVHNFHWNVKGTDFFNVHKATEEIYEEFADMFDDLAERIVQ

SEQ ID NO 2   61  LGHHPLVTLSEALKLTRVKEETKTSFHSKDIFKEILGDYKHLEKEFKELSNTAEKEGDKV
SEQ ID NO 5   61  LGHHPLVTLSEALKLTRVKDETKTSFHSKDIFKEILGDYKHLEKEFKELSNTAEKEGDKV
SEQ ID NO 6   61  LGHHPLVTLSEAIKLTRVKEETKTSFHSKDIFKEILEDYKYLEKEFKELSNTAEKEGDKV

SEQ ID NO 2  121  TVTYADDQLAKLQKSIWMLEAHLA*
SEQ ID NO 5  121  TVTYADDQLAKLQKSIWMLEAHLA*
SEQ ID NO 6  121  TVTYADDQLAKLQKSIWMLQAHLA*
```

ENRICHMENT PROCESS FOR _H. PYLORI_ NEUTROPHIL ACTIVATING PROTEIN (NAP) UTILIZING METAL CHELATE CHROMATOGRAPHY

The invention relates to the NAP protein of _Helicobacter pylori_.

BACKGROUND

_Helicobacter pylori_ is a Gram-negative spiral bacterium which infects the human stomach. It is believed that over 50% of the world's population harbour the bacterium.

Clinical isolates of _H. pylori_ can be characterised by the expression of a vacuolating cytotoxin (VacA), which induces vacuole formation in epithelial cells, and an immunodominant cytotoxin-associated antigen (CagA). Type I strains, which predominate in patients with ulcers or cancer, express both of these proteins, whereas type II strains express neither.

Various antigenic proteins have been described for _H. pylori_, (e.g. references 1&2) including its urease, VacA, flagella proteins, and adhesins. A protein known as NAP, (neutrophil activating protein (3,4)), which is found in both type I and II strains, appears to be protective when tested in the _H. pylori_ mouse model (5).

NAP is a homodecamer of 15 kDa subunits (6), and it has been proposed that the multimeric complex has a ring-shaped structure which spontaneously forms hexagonal paracrystalline structures. The assembled protein appears to interact with glycosphingolipid receptors of human neutrophils (7).

Based on homology with bacterioferritins, it has been suggested that NAP may act as an iron buffer (3). However, the presence of neither iron nor heme has been detected to date. The protein has also been reported to be a $Na^+/H^+$ antiporter (8).

As its name suggests, NAP promotes activation and adhesion of neutrophils to endothelial cells. Whilst it is has been suggested that this function is unlikely to be related to its intracellular function (3), the proadhesive activity can be neutralised by antiserum (6). Since neutrophil activation and adhesion to endothelial cells constitute inflammation mechanisms, and since _H. pylori_ is responsible for stomach inflammation, it seems likely that NAP represents the factor, or a factor, of _H. pylori_ responsible for inflammation, probably at an early stage of gastric ulcer disease when an abundant accumulation of neutrophils in the superficial gastric mucosa is observed.

A protocol for the purification of the NAP decamer from _H. pylori_ has been described (6), involving agarose chromatography, molecular sieving and ion-exchange chromatography. This gave a yield of 72%. Recombinant NAP production in _E. coli_ has also been reported (7). The gene was cloned into plasmid pTrxFus to produce a thioredoxin fusion protein. Protein was then purified in the same way as the native protein. The N-terminal thioredoxin was reported not to affect the biological activity of NAP.

There remains, however, a need for pure NAP without the presence of cloning artefacts, fusion domains or the like. It is therefore an object of the invention to provide a process for the purification of native NAP. It is a further object that this process should be straightforward, easily scalable and economically feasible. It is a further object that the process should provide a highly pure protein.

We have now found that NAP has a surprisingly high aqueous solubility, remaining soluble even at 80% ammonium sulphate saturation.

DESCRIPTION OF THE INVENTION

According to the present invention, there is provided a process for enriching the presence of _H. pylori_ NAP in a mixture of proteins, comprising the step of salting-out other proteins.

The salting-out step leaves the majority of NAP in soluble form. Although any suitable salt can be used, it is preferred to use ammonium sulphate. The final salt concentration is preferably 50% saturation or more (eg. 60%, 70%, 80% or more). The salting-out step preferably precipitates at least 50% of the proteins present in the mixture (eg. 60%, 70%, 80% or more).

Because of the surprisingly high solubility of NAP, this salting-out step alone removes the majority of proteins, considerably enriching the presence of NAP.

The resulting mixture of soluble proteins, enriched for NAP, may then be subjected to further enrichment. It is preferred to clarify the mixture first, however, in order to remove material precipitated in the salting-out step. This is typically achieved by filtration or, preferably, by centrifugation.

A suitable step for further enrichment utilises metal chelate chromatography (9). Any suitable immobilised metal ion can be used (eg. zinc, cobalt, copper), but nickel is preferred.

In a preferred embodiment, therefore, the invention provides a process for the purification of _H. pylori_ NAP from a protein mixture, comprising the steps of salting-out and metal chelate chromatography. This provides a simple two-step purification scheme for NAP.

By "purification" it is meant that NAP forms at least 75% (by weight) of the resulting mixture (eg. 80%, 85%, 90%, 95%, 97%, 99% or more).

The protein mixture may be any suitable source of NAP protein. Examples include _H. pylori_ bacteria themselves, or other hosts which express the gene encoding _H. pylori_ NAP (such as transformed bacteria). These are preferably lysed or disrupted prior to NAP enrichment/purification in order to allow access to their cytoplasmic components (eg. sonication, French press, Hughes press, enzymatic lysis, grinding, freeze/thaw etc).

Preferred conditions and reagents for performing the processes of the invention are those set out in the examples below (eg. bacterial strains, vectors, restriction enzymes, culture media, temperatures, buffers, analytical methods etc.). For instance, in order to remove low molecular weight components, it is preferred to include at least one step of dialysis during the enrichment/purification process.

According to the invention, there is also provided a process for enrichment or purification of NAP from a recombinant host, wherein said NAP has the same sequence as NAP as naturally occurring in _H. pylori_. The purified or enriched protein is free from amino acid sequences typically introduced during the process of recombination or recombinant expression (eg. polyhistidine tags, thioredoxin fusions, GST fusions, intein-terminal sequences etc.).

According to the invention, there is further provided a process for the preparation of a diagnostic agent or therapeutic agent (eg. an immunogenic composition or vaccine), comprising enrichment/purification of NAP as described above, followed by suitable formulation. For agents to be administered to animals, for instance, this might involve formulating the NAP into a physiologically acceptable buffer. For an immunogenic composition or vaccine, this might include the addition of an adjuvant, for instance. For a diagnostic reagent, this might involve the addition of a detectable label to NAP (eg. a radioactive or fluorescent label). These formulation steps are well within the capability of the skilled worker.

According to a further aspect of the invention, there is provided NAP obtainable according to any of the above processes.

There is also provided NAP having the amino acid sequence shown in FIG. 3 as SEQ ID 2.

In addition, the invention provides fragments of NAP according to the invention, wherein said fragments retain one or more of the following functions: (a) the ability to activate neutrophils; (b) the ability to bind a NAP-specific antibody (eg. the fragment retains one or more epitopes of full-length NAP).

Furthermore, the invention provides nucleic acid (eg. DNA or RNA) encoding said NAP or said fragments of NAP.

There is also provided a therapeutic or diagnostic agent comprising NAP (or fragments of NAP) according to the invention. This is preferably an immunogenic composition, such as a vaccine.

In preferred embodiments, the diagnostic or therapeutic agents of the invention comprise additional *H. pylori* proteins or antigens. For example, the compositions might comprise VacA (vacuolating cytotoxin) and/or CagA (cytotoxin-associated antigen) and/or urease proteins in addition to NAP.

Vaccines according to the invention may either be prophylactic (ie. to prevent infection) or therapeutic (ie. to treat disease after infection).

Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid.

Preferred adjuvants to enhance effectiveness of the composition include, but are not limited to: (1) aluminium salts (alum), such as aluminium hydroxide, aluminium phosphate, aluminium sulphate, etc; (2) oil-in-water emulsion formulations (with or without other specific immunostimulating agents such as muramyl peptides or bacterial cell wall components), such as for example (a) MF59™ (WO 90/14837), containing 5% Squalene, 0.5% Tween™ 80, and 0.5% Span 85 (optionally containing various amounts of MTP-PE, although not required) formulated into submicron particles using a microfluidizer (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ may be used or particles generated therefrom such as ISCOMs (immunostimulating complexes); (4) Freund's complete and incomplete adjuvants (CFA & IFA); (5) cytokines, such as interleukins (eg. IL-1, IL-2, IL-4, IL-5, IL-6, IL-7, IL-12, etc.), interferons (eg. IFNγ), macrophage colony stimulating factor (M-CSF), tumor necrosis factor (TNF), etc; and (6) other substances that act as immunostimulating agents to enhance the efficacy of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (eg. the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvanticity effect, as discussed above.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally eg. by injection, either subcutaneously or intramuscularly. They may also be administered to mucosal surfaces (eg. oral or intranasal), or in the form of pulmonary formulations, suppositories, or transdermal applications. Dosage treatment may be a single dose schedule or a multiple dose schedule. The vaccine may be administered in conjunction with other immunoregulatory agents.

NAP according to the invention can also be used in immunoassays to detect antibody levels (or, conversely, anti-NAP antibodies can be used to detect antigen levels). Immunoassays based on well defined, recombinant antigens can be developed to replace invasive diagnostics methods. Antibodies to NAP within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

The invention also provides kits suitable for immunodiagnosis. These contain the appropriate labeled reagents and are constructed by packaging the appropriate materials, including the compositions of the invention, in suitable containers, along with the remaining reagents and materials (eg. suitable buffers, salt solutions, etc.) required for the conduct of the assay, as well as suitable set of assay instructions.

According to the invention, there is also provided a process for detecting antibodies against NAP in a biological sample, comprising the step of contacting NAP according to the invention with said biological sample.

According to the invention, there is further provided a method of immunising an animal, comprising the administration of NAP according to the invention. This NAP is preferably in the form of a vaccine composition.

As an alternative to protein-based vaccines, DNA vaccination may be employed [eg. Robinson & Torres (1997) Seminars in Immunology 9:271–283; Donnelly et al. (1997) Annu Rev Immunol 15:617–648]. Accordingly, rather than comprise NAP, the vaccines of the invention might comprise nucleic acid encoding NAP.

The invention further provides a protein comprising the amino acid sequence shown in FIG. 3 as SEQ ID 2. This protein may be used in the same way as NAP according to the invention.

DESCRIPTION OF THE DRAWINGS

FIG. 1 shows the complete sequence of the gene encoding NAP in strain CCUG (SEQ ID NO:1), which was cloned into plasmid pSM214G to give pSM214-NAP. The Figure also shows the sequence (SEQ ID NO: 9) in the plasmid vector flanking the 5' end of the gene (lower case) and the deduced amino acid sequence (SEQ ID NO: 2).

Figure 2:
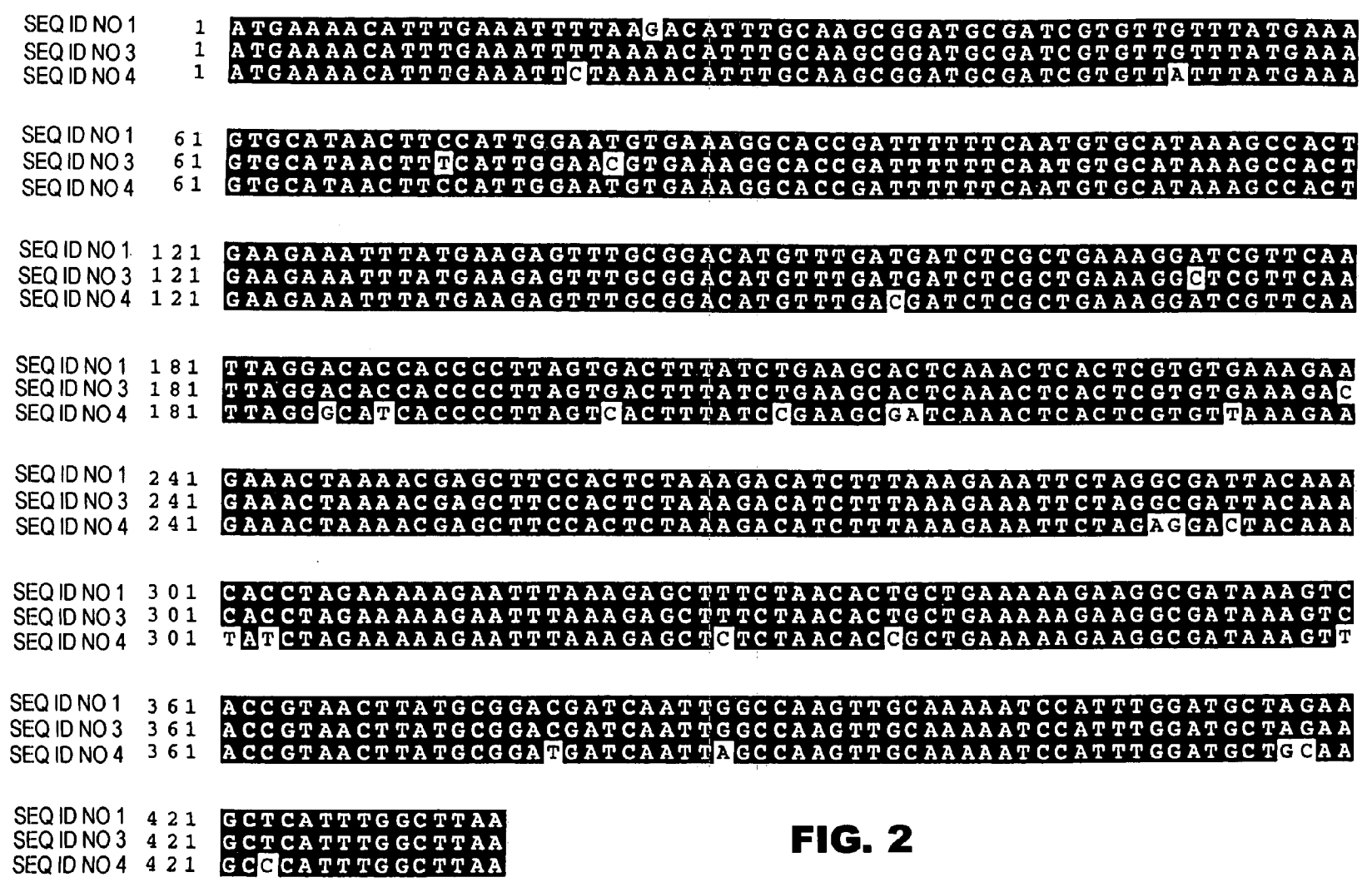

FIG. 2 shows a comparison of the nucleotide sequence of the cloned NAP (SEQ ID NO: 1) with that in references 6 (SEQ ID NO: 3) and 8 (SEQ ID NO: 4). FIG. 3 shows, inter alia, amino acid differences (SEQ ID NO:2) at residues 8, 58 & 80 (in comparison with reference 6 (SEQ ID NO: 5)) and residues 8, 73, 97, 101 & 140 (in comparison with reference 8 (SEQ ID NO: 6), deduced from the whole genome sequence).

EXAMPLES

The practice of the present invention will employ, unless otherwise indicated, conventional techniques of molecular biology, microbiology, recombinant DNA, and immunology, which are within the skill of the art. Such techniques are explained fully in the literature eg. *Molecular Cloning; A Laboratory Manual, Second Edition* (Sambrook, 1989); *DNA Cloning, Volumes I and ii* (ed. Glover 1985); *Oligonucleotide Synthesis* (ed. Gait 1984); *Nucleic Acid Hybridization* (ed. Hames & Higgins 1984); *Transcription and Translation* (ed. Hames & Higgins 1984); *Animal Cell Culture* (ed. Freshney 1986); *Immobilized Cells and Enzymes* (IRL Press, 1986); *A Practical Guide to Molecular Cloning* (Perbal, 1984); the *Methods in Enzymology* series (Academic Press, Inc.), especially volumes 154 & 155; *Gene Transfer Vectors for Mammalian Cells* (ed. Miller & Calos 1987, Cold Spring Harbor Laboratory); *Immunochemical Methods in Cell and Molecular Biology* (ed Mayer & Walker, 1987); *Protein Purification: Principles and Practice* (Scopes, 1987); *Handbook of Experimental Immunology, Volumes I–IV* (ed. Weir & Blackwell 1986).

Cloning of the Gene Encoding NAP

The gene shown in FIG. 1 was amplified from the CCUG chromosome using the following PCR primers, which also introduced SacI and HindIII restriction sites:

5'-ctcgagctctagagggtattaataatgaaaacattgaat-3' (SEQ ID NO: 7)

5'-cccttaagcttttaagqcaaatgagcttc-3' (SEQ ID NO: 8)

The amplification product was digested with SacI and HindIII and ligated into plasmid pSM214G [10] which had been digested with the same two enzymes. This plasmid is a shuttle expression vector between *E. coli* and *B. subtilis*. As can be seen from FIG. 1, the recombinant gene is expressed under the control of a constitutive promoter and a ribosome binding site, which function in both *E. coli* and *B. subtilis*.

The ligated plasmid was used to transform *E. coli* and positive clones were selected on chloramphenicol plates. A plasmid from one positive clone ("pSM214-NAP") was isolated and characterised. Glycerol batches of this clone were stored at –80° C.

In addition, the plasmid was used to transform *B. subtilis*, which was also stored as glycerol batches at –80° C.

Preliminary Expression Analysis

Single colonies of transformed *E. coli* or *B. subtilis* strains were inoculated into 4 ml LB-CAP medium (ie. LB medium +20 μg/ml chloramphenicol) and cultured to 14 hours at 37° C. Control strains were grown containing the transformation vector without the NAP insert.

Figure 4A:
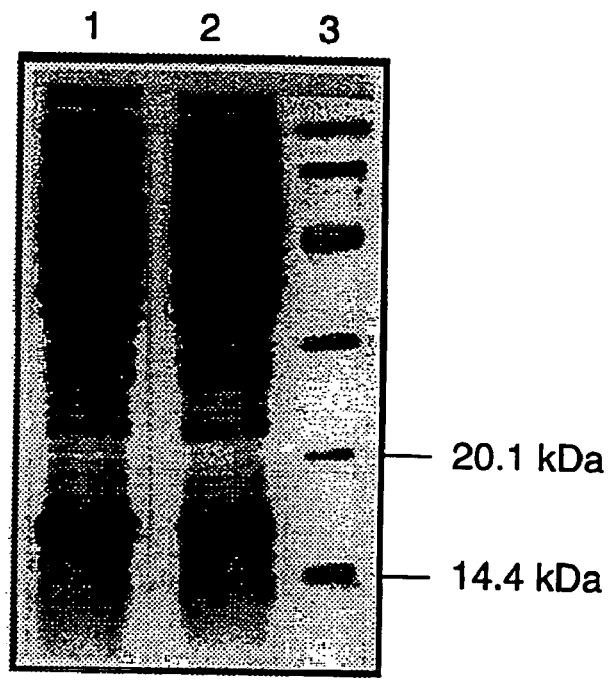
FIG. 4 shows SDS-PAGE (A) and Western blot (B) of total cell proteins from *E. coli*. Lane 1: total extract from transformed cells; lane 2: negative control; lane 3: low MW markers.
Figure 4B:
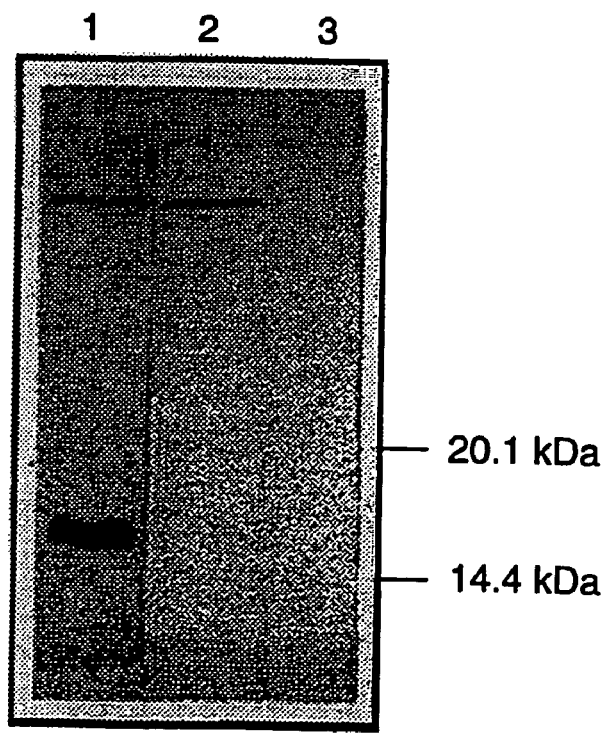

*E. coli* cultures were harvested and resuspended in SDS-PAGE loading sample buffer. *B. subtilis* cultures were harvested, treated with 0.3 mg/ml lysozyme (30 minutes, 37° C.), and then 3×SDS-PAGE loading sample buffer was added. The samples were incubated for 5 minutes at 95° C. and separated by SDS-PAGE, after which the proteins were analysed by Coomassie blue staining and Western blot. The blot was visualised with an antiserum obtained by immunising a rabbit with a NAP-thioredoxin fusion (FIG. 4).

The transformed bacteria clearly express a 15 kDa protein not present in the non-transformed strains, as shown by rabbit antiserum.

Cell Culture and Lysis

Single colonies of transformed *E. coli* or *B. subtilis* were inoculated in 5 ml LB-CAP and incubated for 37° C. for 10 hours. The 5 ml cultures were then used to inoculate 2 liter flasks containing 500-ml LB-CAP. After 14 hours incubation at 37° C. on a rotary shaker (250 cycles/min), the cells were harvested by centrifugation at 6000 g for 20 minutes at 4° C. Cell pellets were disrupted using either sonication or a French press.

For sonication, the pellets were resuspended in 8 ml buffer A (20 mM Tris-HCl, pH 7.8) supplemented with 0.3 mg/ml lysozyme. After incubation on ice (10 minutes) and then at 37° C. (7 minutes), 35 µl of a 2 mg/ml DNaseI solution (Sigma D-4263) was added. The samples were put on ice and sonicated extensively until disappearance of viscosity (Branson sonifier 450, medium tip, duty cycle 50, output control 5, approx. 25×2 minute cycles of 1 minute sonication/1 minute on ice). The lysate was brought to 14 ml with buffer A and centrifuged at 20000 g for 20 minutes at 4° C. Supernatant (soluble total extract) and pellets (insoluble total extract) were separated and either used immediately or stored at −20° C.

For French press disruption, cells were resuspended in 15 ml buffer A and lysed by three passages in the press. The soluble proteins were collected by centrifugation at 12000 g for 30 minutes at 4° C. and the supernatant was brought to 28 ml with buffer A.

Figure 5A:
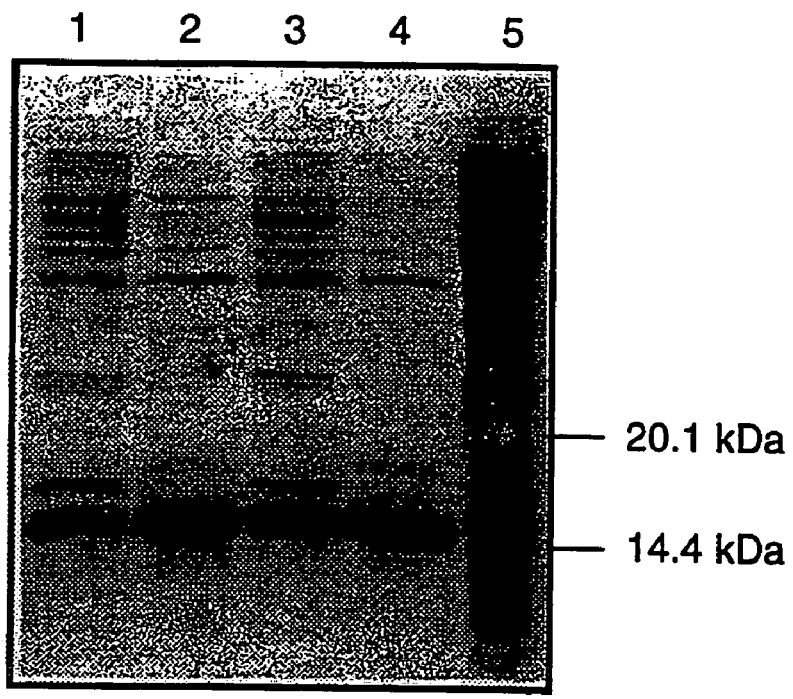
FIG. 5 shows Poinceau staining (A) and Western blot (B) of transformed *E. coli*. Lane 1: soluble extract; lane 2: insoluble extract; lane 3: low MW markers.
Figure 5B:
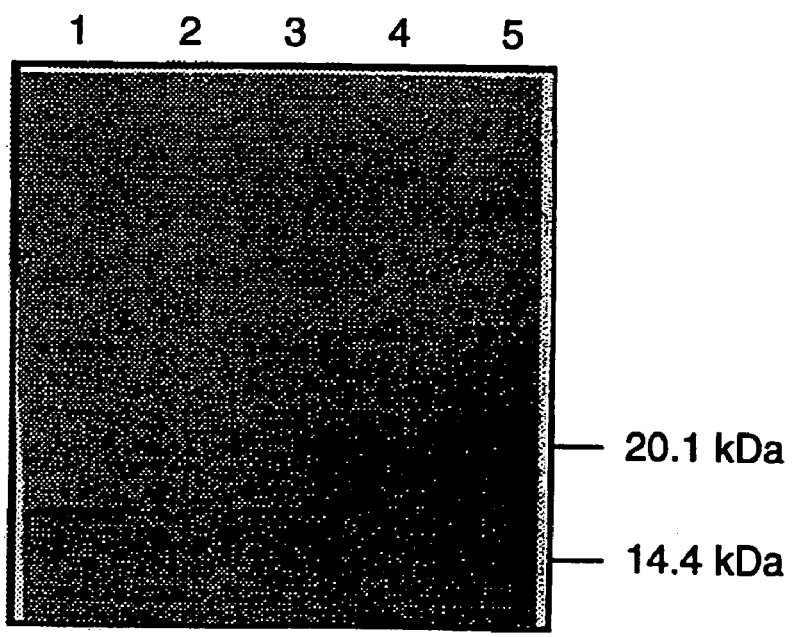
Figure 6A:
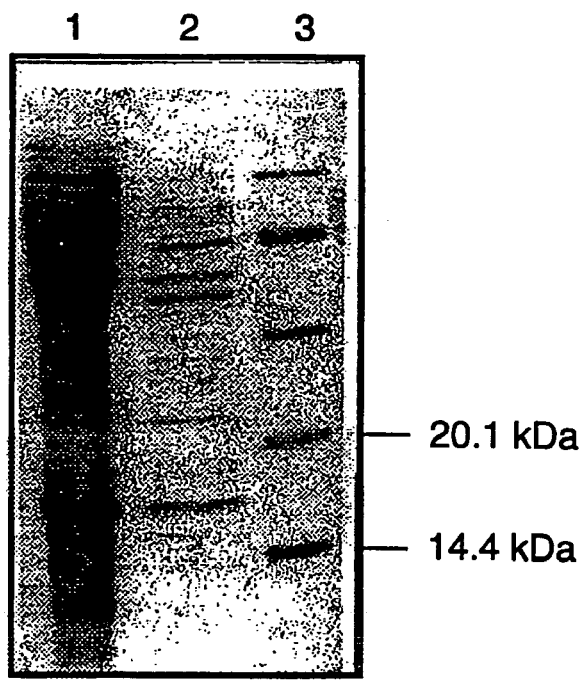
FIG. 6 shows Poinceau staining (A) and Western blot (B) of transformed *B. subtilis*. Lanes 1 & 2: strain SMS118, soluble & insoluble extracts, respectively; Lanes 3 & 4: strain SMS300, soluble & insoluble extracts, respectively; lane 5: negative control (*B. subtilis* transformed with pSM214 without the NAP insert).
Figure 6B:
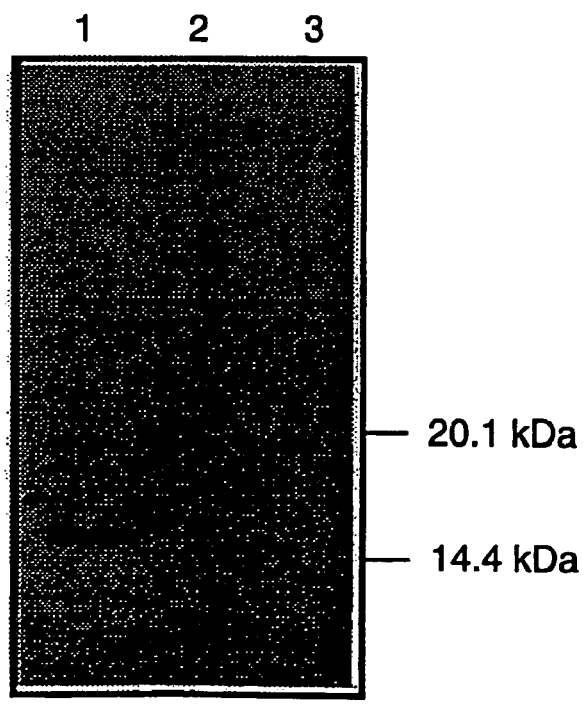

SDS-PAGE analysis of the soluble and insoluble total extracts (FIGS. 5 & 6) show that the serum raised against NAP reacts only with the soluble fraction, indicating that NAP is fully soluble in buffer A.

Protein Purification

*B. subtilis* total soluble proteins were diluted with buffer A to give a total protein concentration of 8 mg/ml (Bradford). Ammonium sulphate was added to a final concentration of 60% saturation and the salting-out process was left overnight at 4° C. with gentle stirring. Precipitated proteins were removed by centrifugation at 12000 g for 30 minutes at 4° C. and the supernatant was dialysed overnight against buffer A.

The dialysed solution was loaded onto a nickel-activated chelating sepharose FF column (1×8 cm) equilibrated with buffer A. The column was washed with buffer A+200 mM NaCl. Protein elution was carried out with a 46 ml linear gradient of 0–40 mM imidazole, followed by a second 10 ml gradient of 40–100 mM imidazole (flow rate 0.5 ml/min). Elution was then continued with 25 ml 100 mM imidazole.

Fractions were analysed by SDS-PAGE, and those containing NAP were pooled and dialysed against PBS buffer (pH 7–7.5).

NAP was purified from *E. coli* in the same way, except that the salting-out procedure used 80% saturation.

Purity

From 1 liter of culture, the results of the purifications were:

| Bacterium | NAP (mg) | Purity (SDS-PAGE) |
|---|---|---|
| *B. subtilis* | 10 | 90% |
| *E. coli* | 30 | 95% |

Figure 8:
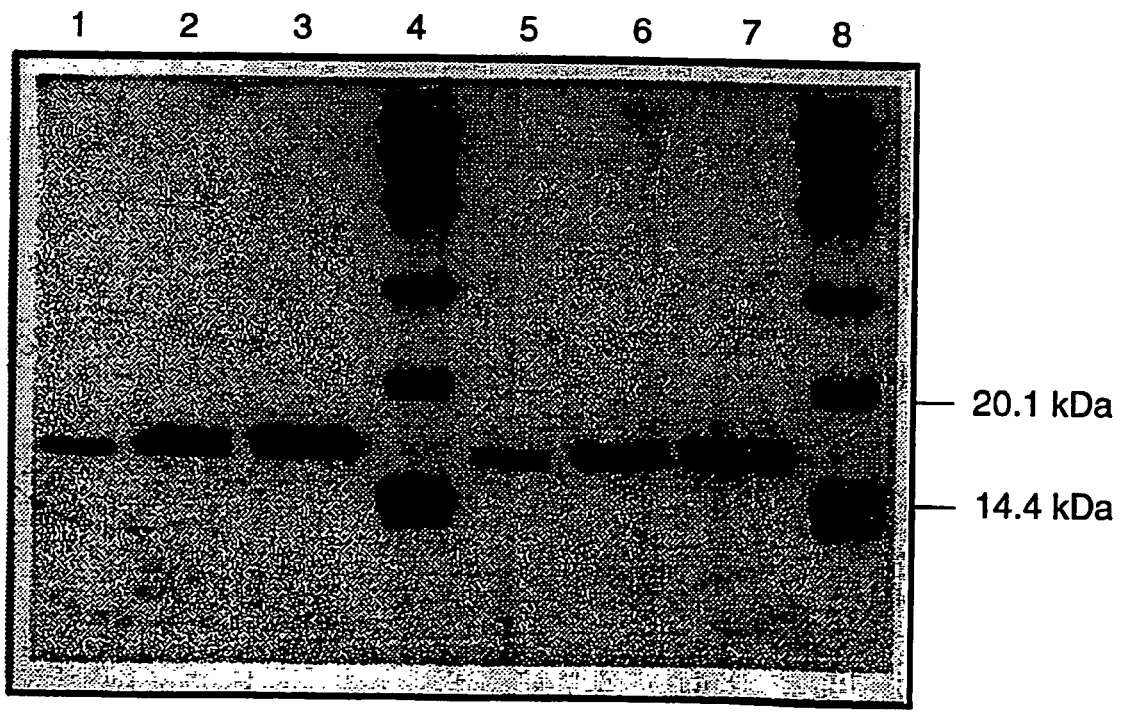
FIG. 8 shows the purity of the final NAP product. Lanes 1–3 contain material purified from *E. coli*; lanes 507 contain material purified from *B. subtilis* (SMS118). From left to right, these lanes contain 1 μg, 2 μg & 3 μg protein, respectively. Lanes 4 & 8 are markers.

An indication of purity, by Coomassie Blue staining, is given in FIG. 8. The material from *E. coli* appears to slightly purer. A yield of 80% is estimated, by densitometric analysis.

Salting-Out

Figure 7:
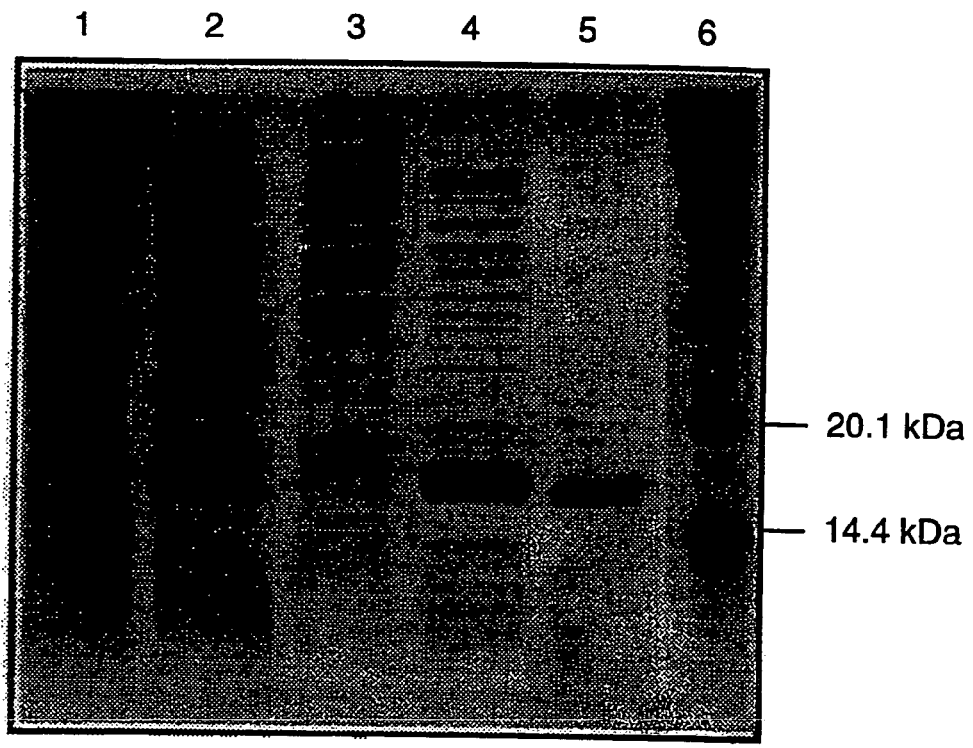
FIG. 7 illustrates the effect of salting-out by ammonium sulphate. Lanes 1 & 2: 60% saturation, pellet & supernatant (from *E. coli*), respectively; lanes 3 & 4: increased saturation from 60% to 80% (pellet & supernatant, respectively); lane 5: purified NAP; lane 6: markers.

NAP appears to be soluble even at very high concentrations of ammonium sulphate. As shown in FIG. 7, NAP remains soluble even at 80% saturation. Lane 4 of the gel shows that salting-out alone gives a high degree of purification.

Multimeric Assembly

The ability of purified NAP to assemble into a multimeric form was investigated using size exclusion chromatography (non-reducing, non-denaturing). NAP was loaded on a Sepharose 12 HR 10/30 column equilibrated in buffer (25 mM Tris-HCl, 150 mM NaCl, pH 7.8) and eluted at 0.5 ml/min. Regardless of the source of the NAP, the protein eluted in a single peak having the same retention time as yeast alcohol dehydrogenase (MW 150 kDa), indicating a decameric structure [6].

N-Terminal Sequencing

N-terminal sequencing of purified NAP was carried out using a Beckmann LF 3000 protein sequencer equipped with on-line RP-HPLC analysis of PTH amino acids. The 10 amino acids sequenced were identical to those deduced from the gene sequence shown in FIG. 1.

Comparison with Native Protein

*H. pylori* CCUG cells were collected from the surface of blood agar plates, washed in ice-cold PBS, and resuspended in lysis buffer (20 mM Tris-HCl, 2.5 mM EDTA, 0.3 mg/ml lysozyme, pH 7.8). The cell suspension was incubated at 37° C. for 20 minutes, sonicated, and centrifuged at 20000 g for 40 minutes. The supernatant (soluble proteins) was stored at −20° C. until use.

The retention time in gel filtration chromatography for NAP purified from *E. coli* or from *B. subtilis* was identical to that in the *H. pylori* soluble protein extract.

It will be understood that the invention is described above by way of example only and modifications may be made whilst remaining within the scope and spirit of the invention.

REFERENCES

1. Telford J L, Covacci A, Rappuoli R, Ghiara P (1997) Immunobiology of *Helicobacter pylori* infection. *Curr Opin Immunol* 9:498–503.
2. Telford J L, Covacci A, Ghiara P, Montecucco C, Rappuoli R (1994) Unravelling the pathogenic role of *Helicobacter pylori* in peptic ulcer: potential new therapies and vaccines. *TIBTECH* 12:420–426.
3. Evans D J, Evans D G, Lampert H C, Nakano H (1995) Identification of four new prokaryotic bacterioferritins, from *Helicobacter pylori, Anabaena variabilis, Bacillus subtilis* and *Treponema pallidum*, by analysis of gene sequences. *Gene* 153:123–127.
4. WO96/01272 & WO96/01273, especially SEQ ID NO:6; see also WO97/25429.
5. Marchetti M, Aricò B, Burroni D, Figura N, Rappuoli R, Ghiara P (1995) Development of a mouse model of *Helicobacter pylori* infection that mimics human disease. *Science* 261:1655–1658.
6. Evans D J, Evans D G, Takemura T, Nakano H, Lampert H C, Graham D Y, Granger D N, Kviety P R (1995) Characterization of a *Helicobacter pylori* Neutrophil-Activating Protein. *Infect Immun* 63(6):2213–2220.
7. Teneberg S, Miller-Podraza H, Lampert H C, Evans D J, Evans D G, Danielsson D, Karlsson K-A (1997) Carbohydrate binding specificity of the neutrophil-activating protein of *Helicobacter pylori*. *J Biol Chem* 272:19067–19071.
8. Tomb J-F et al. (1997) The complete genome sequence of the gastric pathogen *Helicobacter pylori*. *Nature* 388: 539–547.
9. Sulkowski E (1985) Purification of proteins by IMAC. *TIBTECH* 3:1–7.
10. A derivative of pSM214—Bellini et al, *J. Biotechnol.* 18:177–192—in which the Amp gene has been replaced with a multi-cloning site.

---

The invention claimed is:

1. A process for enriching the presence of *H. pylori* NAP (neutrophil activating protein) in a mixture of proteins comprising said NAP, said process comprising the steps of:
    salting-out other proteins from said mixture of proteins thereby producing a supernatant comprising said NAP, wherein the salt concentration of the mixture of proteins is at least 50% saturation;
    subjecting said supernatant to metal chelate chromatography, and
    eluting said NAP from said metal,
wherein said step of eluting yields a mixture of proteins enriched in NAP content of the total protein and wherein said NAP is not a fusion protein.

2. The process according to claim 1, wherein said metal is nickel.

3. The process according to claim 2, wherein said NAP is recombinant NAP.

4. The process according to claim 1, wherein said NAP is recombinant NAP.

5. A process for the purification of *H. pylori* NAP (neutrophil activating protein) from a protein mixture comprising said NAP, said process comprising the steps of:
    salting-out other proteins from said protein mixture to produce a supernatant comprising said NAP wherein the salt concentration of the protein mixture is at least 50% saturation;
    subjecting said supernatant to metal chelate chromatography; and
    eluting said NAP from said metal,
wherein said NAP is not a fusion protein, thereby obtaining purified NAP.

6. The process according to claim 5, wherein said metal is nickel.

7. The process according to claim 6, wherein said NAP is recombinant NAP.

8. The process according to claim 5, wherein said NAP is recombinant NAP.

9. A process for enriching the presence of recombinant *H. pylori* NAP (neutrophil activating protein) in a mixture of proteins comprising said recombinant NAP, said process comprising the steps of:
    salting-out other proteins from said mixture of proteins thereby producing a supernatant comprising said recombinant NAP, wherein the salt concentration of the mixture of proteins is at least 50% saturation;
    subjecting said supernatant to metal chelate chromatography; and
    eluting said recombinant NAP from said metal,
wherein said step of eluting yields a mixture of proteins enriched in NAP content of the total protein, wherein said recombinant NAP is a fusion protein, and wherein enrichment of said recombinant NAP by the step of metal chelate chromatography is not mediated by a fusion domain of said recombinant NAP.

10. The process according to claim 9, wherein said metal is nickel.

11. A process for the purification of recombinant *H. pylori* NAP (neutrophil activating protein) from a protein mixture comprising said recombinant NAP, said process comprising the steps of:
    salting-out other proteins from said protein mixture thereby producing a supernatant comprising said recombinant NAP, wherein the salt concentration of the protein mixture is at least 50% saturation;
    subjecting said supernatant to metal chelate chromatography; and
    eluting recombinant NAP from said metal,
wherein said recombinant NAP is a fusion protein and wherein purification of recombinant NAP by the step of metal chelate chromatography is not mediated by a fusion domain of said recombinant NAP, thereby obtaining purified recombinant NAP.

12. The process according to claim 11, wherein said metal is nickel.

13. A process for enriching the presence of *H. pylori* NAP (neutrophil activating protein) in a mixture of proteins comprising said NAP, said process comprising the steps of salting-out proteins from said mixture of proteins and removing salted-out proteins from said mixture of proteins thereby producing a supernatant comprising said NAP, wherein the salt concentration of the mixture of proteins is at least 80% saturation, and wherein said NAP is recombinant NAP.

* * * * *

SEQUENCE LISTING

<160> NUMBER OF SEQ ID NOS: 13

<210> SEQ ID NO 1
<211> LENGTH: 870
<212> TYPE: DNA
<213> ORGANISM: Momordica charantia

<400> SEQUENCE: 1

```
gcacgagggg gaagactttt tgcaggactg cgatttctgt ttacatcaat ggctgaagaa      60
gggcaagtga ttgcgtgtca taagatagat gaatgggagg gacaattagg aaaatggaag    120
gattctgaga aactggttgt ggtggatttt actgcttcct ggtgcgggcc atgccgggca    180
attgctccat atttcacaga attggctaag aataacccaa atgtcgcttt cctgaaagtc    240
gacgttgacg aattgaacag tgttgctagc aagtgggaga ttaatgcaat gccaacgttt    300
gttttcctga aaaagggaa aataattgag aagatcgttg gtgctgataa agtggggctg    360
tcgaagaaaa tattagagct tagtggaact actcccgctg ctacttctac tgcttagaca    420
gtctgcttgg aggatgtgat ccctctggtg caatggtgat tccgctttgg agtttgatct    480
aattgtggat gaaactgtgt ctaaaagatg ttaattgttt ggcctttttgg gttttcccct    540
tttttaagttt ggatcatgtg cgcacctctc agttgtgatt ctggtgctag aagcttcagg    600
tttcaatgtg gaataaatgg gggcacctgc tctgaaattg aatgacattt ttgcacactt    660
ttcattattc ttctgtaaga acttgaattc actgtttttt tttaatctaa ttcttcgtag    720
cagtacagtg agatgttctt tcagcttgtt tagcaacttc ttaatccctc tcctggcttt    780
tattttctta ttattggaat ggaacttaga agaatcgaag ttgttatgat ttgttaaaag    840
tatttgttgt taaaaaaaaa aaaaaaaaaa                                      870
```

<210> SEQ ID NO 2
<211> LENGTH: 122
<212> TYPE: PRT
<213> ORGANISM: Momordica charantia

<400> SEQUENCE: 2

```
Met Ala Glu Glu Gly Gln Val Ile Ala Cys His Lys Ile Asp Glu Trp
 1               5                  10                  15

Glu Gly Gln Leu Gly Lys Trp Lys Asp Ser Glu Lys Leu Val Val
            20                  25                  30

Asp Phe Thr Ala Ser Trp Cys Gly Pro Cys Arg Ala Ile Ala Pro Tyr
        35                  40                  45

Phe Thr Glu Leu Ala Lys Asn Asn Pro Asn Val Ala Phe Leu Lys Val
    50                  55                  60

Asp Val Asp Glu Leu Asn Ser Val Ala Ser Lys Trp Glu Ile Asn Ala
65                  70                  75                  80

Met Pro Thr Phe Val Phe Leu Lys Lys Gly Lys Ile Ile Glu Lys Ile
                85                  90                  95

Val Gly Ala Asp Lys Val Gly Leu Ser Lys Ile Leu Glu Leu Ser
            100                 105                 110
```

```
Gly Thr Thr Pro Ala Ala Thr Ser Thr Ala
        115                 120
```

```
<210> SEQ ID NO 3
<211> LENGTH: 574
<212> TYPE: DNA
<213> ORGANISM: Catalpa speciosa

<400> SEQUENCE: 3
gcacgagggc ataaatacct tgtaattggg gattttttcgg agtaaaaaag ggaaatcgga    60
aaatggcttc ttcagaagag ggacaagtga tcggttgcca ctccgtcgac gagtggaagg   120
agcagttcca gaagggtgtt gactctaaga aactggtggt aatagacttc acggcttcct   180
ggtgcggacc atgccgtttc attgctccaa tcttggctga gatggccaag aagacacccc   240
atgtcatatt cctgaaagtc gacgtggatg aactcaagac tgttgctgag gaattcaaag   300
tggaggctat gccgaccttc gtgttcctca aggaagggaa agaagtggaa aggcttgtgg   360
gagcaaggaa ggaggaattg caggccacag ttgagaaaca tggcgctatc actgcttgat   420
gctgtttcaa tgtttagtta tgtaatatat gatgatgctt ggaataataa tgtcttaagt   480
tatccagatc gtatgtgact gacgtttctg ttgttatgtg gattgttatt gttaatgtaa   540
tgtaatggag tgtcttaaaa aaaaaaaaaa aaaa                               574
```

```
<210> SEQ ID NO 4
<211> LENGTH: 118
<212> TYPE: PRT
<213> ORGANISM: Catalpa speciosa

<400> SEQUENCE: 4

Met Ala Ser Ser Glu Glu Gly Gln Val Ile Gly Cys His Ser Val Asp
  1               5                  10                  15
Glu Trp Lys Glu Gln Phe Gln Lys Gly Val Asp Ser Lys Lys Leu Val
             20                  25                  30
Val Ile Asp Phe Thr Ala Ser Trp Cys Gly Pro Cys Arg Phe Ile Ala
         35                  40                  45
Pro Ile Leu Ala Glu Met Ala Lys Lys Thr Pro His Val Ile Phe Leu
     50                  55                  60
Lys Val Asp Val Asp Glu Leu Lys Thr Val Ala Glu Glu Phe Lys Val
 65                  70                  75                  80
Glu Ala Met Pro Thr Phe Val Phe Leu Lys Glu Gly Lys Glu Val Glu
                 85                  90                  95
Arg Leu Val Gly Ala Arg Lys Glu Glu Leu Gln Ala Thr Val Glu Lys
            100                 105                 110
His Gly Ala Ile Thr Ala
        115
```

```
<210> SEQ ID NO 5
<211> LENGTH: 738
<212> TYPE: DNA
<213> ORGANISM: Glycine max

<400> SEQUENCE: 5
gcaccaggaa attctttagt tgtaactgac aaagttttct gagaaaataa ggattattat    60
tgagagaatg gctggctcat cggaagaggg acaagtcatt agctgccaca ccgttgaaga   120
atggaacgat caactccaga agggcaacga atccaagaaa ctcattgttg tggattttac   180
tgcttcttgg tgtggaccat gccgtttcat tgcaccattc ttggctgagc tggctaagaa   240
```

```
gttcacaagt gtcatattcc taaaggtgga tgtggacgaa ttaaagagtg tttctcaaga      300
ttgggctatt gaggctatgc ccacttttgt gtttgtgaaa gagggaacgc ttctggacaa      360
agtggtggga gcaaagaagg atgagctgca gcagaaaata cagaaacatg tggcttcagc      420
tagtgcttaa tctagctcac cttcagaaac tttatatatg cgctttcttt tcataatctt      480
gtactagact tatgttggta tttctgttat tgcaccaatc agcttttcaa aggtgatgac      540
tcctatcatc tatttctgaa tagtagtaac tggtcctttc ttccgtctta aataatagtg      600
gatggtgcta tcatgaat cttaattaca tagaccttcc tgttttccct tttagtatta        660
aaaaaaaaaa aaaaaaaaa aaaaaaaaa aaaaaaaaa aaaaaaaaaa aaacaataaa          720
aaaaacaaaa aaaaaaaa                                                    738

<210> SEQ ID NO 6
<211> LENGTH: 120
<212> TYPE: PRT
<213> ORGANISM: Glycine max

<400> SEQUENCE: 6

Met Ala Gly Ser Ser Glu Glu Gly Gln Val Ile Ser Cys His Thr Val
 1               5                  10                  15

Glu Glu Trp Asn Asp Gln Leu Gln Lys Gly Asn Glu Ser Lys Lys Leu
             20                  25                  30

Ile Val Val Asp Phe Thr Ala Ser Trp Cys Gly Pro Cys Arg Phe Ile
         35                  40                  45

Ala Pro Phe Leu Ala Glu Leu Ala Lys Lys Phe Thr Ser Val Ile Phe
     50                  55                  60

Leu Lys Val Asp Val Asp Glu Leu Lys Ser Val Ser Gln Asp Trp Ala
 65                  70                  75                  80

Ile Glu Ala Met Pro Thr Phe Val Phe Val Lys Glu Gly Thr Leu Leu
                 85                  90                  95

Asp Lys Val Val Gly Ala Lys Lys Asp Glu Leu Gln Gln Lys Ile Gln
            100                 105                 110

Lys His Val Ala Ser Ala Ser Ala
        115                 120

<210> SEQ ID NO 7
<211> LENGTH: 601
<212> TYPE: DNA
<213> ORGANISM: Glycine max

<400> SEQUENCE: 7
gcacgagctc tctctctcta gacttagatt ttgtgaatgg ctgaagtgga agagggacag      60
gtcatcggcg tccacaccgt tgatgagtgg aagctgcaac tccagaatgc aaaagactcc     120
aaaaaactga ttgtggtgga ttttactgct tcctggtgtg gtccatgccg ttttatggcc     180
ccagttcttg cagagattgc aaagaaaact cctgaattga tcttcctcaa agtggatgtg     240
gatgaagtga ggcctgttgc tgaggaatat tccattgagg ccatgccaac cttcctcttc     300
ttgaaagatg gcgagatcgt ggacaaggtg gttggtgcta gtaaggatga ccttcaagcc     360
accatagcca agcatgcatc tgctgtttgct gctgcttctt cttcttgaag tgaagtatca     420
taatatgaaa gaagacaaag aataatgcat tttaatgttt tcaagtcagt ttggatgttt     480
tctctatgga cattgagttg gcagaacatc gagtgatgta taaaaataaa attgttgcat     540
tgtcttttt tcgtaaaaaa aaaaaaaaaa aaaaaaaaa aaaaaaaaa aaaaaaaaa          600
``` a                                                                      601

<210> SEQ ID NO 8
<211> LENGTH: 123
<212> TYPE: PRT
<213> ORGANISM: Glycine max

<400> SEQUENCE: 8

Met Ala Glu Val Glu Gly Gln Val Ile Gly Val His Thr Val Asp
1               5                   10                  15

Glu Trp Lys Leu Gln Leu Gln Asn Ala Lys Asp Ser Lys Lys Leu Ile
                20                  25                  30

Val Val Asp Phe Thr Ala Ser Trp Cys Gly Pro Cys Arg Phe Met Ala
            35                  40                  45

Pro Val Leu Ala Glu Ile Ala Lys Lys Thr Pro Glu Leu Ile Phe Leu
        50                  55                  60

Lys Val Asp Val Asp Glu Val Arg Pro Val Ala Glu Glu Tyr Ser Ile
65                  70                  75                  80

Glu Ala Met Pro Thr Phe Leu Phe Leu Lys Asp Gly Glu Ile Val Asp
                85                  90                  95

Lys Val Val Gly Ala Ser Lys Asp Asp Leu Gln Ala Thr Ile Ala Lys
            100                 105                 110

His Ala Ser Ala Val Ala Ala Ala Ser Ser Ser
        115                 120

<210> SEQ ID NO 9
<211> LENGTH: 614
<212> TYPE: DNA
<213> ORGANISM: Vernonia mespilifolia

<400> SEQUENCE: 9
gcacgaggct aaataccatt tgaaagctaa aaaaaaatct ttgaattagg ttttcttgaa     60
gaagtttgag aaaaaaaatg gcggaagaag gagttgtaac cggaatccac accgtcgacc    120
agtggaatga gcaacttgag aagcacaagg gaactgacaa attggtggtt gtggatttca    180
ccgcctcatg gtgtggtcct tgccgtgtga ttgcaccaat cttggctgat tttgctaaga    240
agatgcccca tgttaccttc cttaaggttg atgtggatga actcgagagc gttgctcagg    300
agtggtcagt ggaggcaatg ccgactttcc tgtttctcaa gggcggagtg aaagtggaca    360
aggttgtggg tgctaagaaa gacgaacttc atgcctgcat cgtcaagcat tctgctgcta    420
cagtttctgc ttaacgtact acataaatatg attatcttat cagcaactta ttagtctctt    480
ttcggatgtg ttgttgattt gctttgtggt aaaaccttag attttgaata ttgtccttgt    540
aaccttgggt tataacttgc tctttcatct atatgcataa attgaagttg ctgtattaaa    600
aaaaaaaaaa aaaa                                                      614

<210> SEQ ID NO 10
<211> LENGTH: 118
<212> TYPE: PRT
<213> ORGANISM: Vernonia mespilifolia

<400> SEQUENCE: 10

Met Ala Glu Glu Gly Val Val Thr Gly Ile His Thr Val Asp Gln Trp
1               5                   10                  15

Asn Glu Gln Leu Glu Lys His Lys Gly Thr Asp Lys Leu Val Val Val
                20                  25                  30

Asp Phe Thr Ala Ser Trp Cys Gly Pro Cys Arg Val Ile Ala Pro Ile

```
                35                  40                  45

Leu Ala Asp Phe Ala Lys Lys Met Pro His Val Thr Phe Leu Lys Val
 50                  55                  60

Asp Val Asp Glu Leu Glu Ser Val Ala Gln Glu Trp Ser Val Glu Ala
 65                  70                  75                  80

Met Pro Thr Phe Leu Phe Leu Lys Gly Gly Val Lys Val Asp Lys Val
                 85                  90                  95

Val Gly Ala Lys Lys Asp Glu Leu His Ala Cys Ile Val Lys His Ser
                100                 105                 110

Ala Ala Thr Val Ser Ala
            115

<210> SEQ ID NO 11
<211> LENGTH: 114
<212> TYPE: PRT
<213> ORGANISM: Arabidopsis thaliana

<400> SEQUENCE: 11

Met Ala Ser Glu Glu Gly Gln Val Ile Ala Cys His Thr Val Glu Thr
  1               5                  10                  15

Trp Asn Glu Gln Leu Gln Lys Ala Asn Glu Ser Lys Thr Leu Val Val
                 20                  25                  30

Val Asp Phe Thr Ala Ser Trp Cys Gly Pro Cys Arg Phe Ile Ala Pro
                 35                  40                  45

Phe Phe Ala Asp Leu Ala Lys Lys Leu Pro Asn Val Leu Phe Leu Lys
 50                  55                  60

Val Asp Thr Asp Glu Leu Lys Ser Val Ala Ser Asp Trp Ala Ile Gln
 65                  70                  75                  80

Ala Met Pro Thr Phe Met Phe Leu Lys Glu Gly Lys Ile Leu Asp Lys
                 85                  90                  95

Val Val Gly Ala Lys Lys Asp Glu Leu Gln Ser Thr Ile Ala Lys His
                100                 105                 110

Leu Ala

<210> SEQ ID NO 12
<211> LENGTH: 126
<212> TYPE: PRT
<213> ORGANISM: Nicotiana tabacum

<400> SEQUENCE: 12

Met Ala Ala Asn Asp Ala Thr Ser Ser Glu Glu Gly Gln Val Phe Gly
  1               5                  10                  15

Cys His Lys Val Glu Glu Trp Asn Glu Tyr Phe Lys Lys Gly Val Glu
                 20                  25                  30

Thr Lys Lys Leu Val Val Val Asp Phe Thr Ala Ser Trp Cys Gly Pro
                 35                  40                  45

Cys Arg Phe Ile Ala Pro Ile Leu Ala Asp Ile Ala Lys Lys Met Pro
 50                  55                  60

His Val Ile Phe Leu Lys Val Asp Val Asp Glu Leu Lys Thr Val Ser
 65                  70                  75                  80

Ala Glu Trp Ser Val Glu Ala Met Pro Thr Phe Val Phe Ile Lys Asp
                 85                  90                  95

Gly Lys Glu Val Asp Arg Val Val Gly Ala Lys Lys Glu Glu Leu Gln
                100                 105                 110

Gln Thr Ile Val Lys His Ala Ala Pro Ala Thr Val Thr Ala
            115                 120                 125
```

```
<210> SEQ ID NO 13
<211> LENGTH: 118
<212> TYPE: PRT
<213> ORGANISM: Ricinus communis

<400> SEQUENCE: 13

Met Ala Ala Glu Glu Gly Gln Val Ile Gly Cys His Thr Val Glu Ala
  1               5                  10                  15

Trp Asn Glu Gln Leu Gln Lys Gly Asn Asp Thr Lys Gly Leu Ile Val
                 20                  25                  30

Val Asp Phe Thr Ala Ser Trp Cys Gly Pro Cys Arg Phe Ile Ala Pro
             35                  40                  45

Phe Leu Ala Glu Leu Ala Lys Lys Leu Pro Asn Val Thr Phe Leu Lys
         50                  55                  60

Val Asp Val Asp Glu Leu Lys Thr Val Ala His Glu Trp Ala Val Glu
 65                  70                  75                  80

Ser Met Pro Thr Phe Met Phe Leu Lys Glu Gly Lys Ile Met Asp Lys
                     85                  90                  95

Val Val Gly Ala Lys Lys Asp Glu Leu Gln Gln Thr Ile Ala Lys His
                100                 105                 110

Met Ala Thr Ala Ser Thr
            115
```